United States Patent
Puckett et al.

(10) Patent No.: US 9,404,904 B2
(45) Date of Patent: *Aug. 2, 2016

(54) METHODS AND SYSTEMS FOR NON-DESTRUCTIVE INSPECTION

(71) Applicant: The Boeing Company, Seal Beach, CA (US)

(72) Inventors: Edward L. Puckett, Renton, WA (US); Andrej M. Savol, Lake Tapps, WA (US)

(73) Assignee: The Boeing Company, Chicago, IL (US)

( * ) Notice: Subject to any disclaimer, the term of this patent is extended or adjusted under 35 U.S.C. 154(b) by 275 days.

This patent is subject to a terminal disclaimer.

(21) Appl. No.: 14/179,461

(22) Filed: Feb. 12, 2014

(65) Prior Publication Data

US 2015/0122055 A1 May 7, 2015

Related U.S. Application Data

(60) Provisional application No. 61/900,239, filed on Nov. 5, 2013.

(51) Int. Cl.
| | |
|---|---|
| *G01N 33/00* | (2006.01) |
| *G01N 27/90* | (2006.01) |
| *G01N 29/04* | (2006.01) |
| *G01N 29/06* | (2006.01) |

(Continued)

(52) U.S. Cl.
CPC ............... *G01N 33/00* (2013.01); *G01N 27/90* (2013.01); *G01N 29/04* (2013.01); *G01N 29/0654* (2013.01); *G01N 29/225* (2013.01); *G01N 29/265* (2013.01); *A61B 5/065* (2013.01)

(58) Field of Classification Search
CPC ....... G01N 33/00; G01N 27/90; G01N 29/04; G01N 29/0654; G01N 29/445; G01N 29/265
USPC ............................... 73/865, 601, 865.8; 345/8
See application file for complete search history.

(56) References Cited

U.S. PATENT DOCUMENTS

| | | | |
|---|---|---|---|
| 8,892,252 B1* | 11/2014 | Troy ...................... | G01B 11/14 700/213 |
| 2004/0183751 A1* | 9/2004 | Dempski .............. | G02B 27/017 345/8 |

(Continued)

FOREIGN PATENT DOCUMENTS

| | | |
|---|---|---|
| EP | 1 480 006 | 11/2004 |
| WO | WO 2007/021541 | 2/2007 |

OTHER PUBLICATIONS

ARToolKit Documentation, Tutorials 1-3 from http://www.hitl.washington.edu/artoolkit/documentation, downloaded Jan. 29, 2014.

(Continued)

*Primary Examiner* — Lisa Caputo
*Assistant Examiner* — Nathaniel T Woodward
(74) *Attorney, Agent, or Firm* — DASCENZO Intellectual Property Law, P.C.

(57) ABSTRACT

Disclosed non-destructive inspection methods comprise non-contact determination of the location of a non-destructive inspection probe and identification of the location on a test structure where test data is acquired by the probe. Determination may include capturing the positions of the probe and the test structure with one or more electronic cameras. Identification may include associating the acquired test data with the location of the probe relative to the test structure. Further, methods may comprise visualization of the test data relative to the identified location. Disclosed non-destructive inspection systems comprise a probe, one or more electronic cameras, a computer, and a display, together configured to determine the location of the probe, to acquire test data with the probe, to identify a location on a test structure associated with the test data, and to visualize the test data in relation to the test structure.

26 Claims, 2 Drawing Sheets

(51) Int. Cl.
*G01N 29/22* (2006.01)
*G01N 29/265* (2006.01)
*A61B 5/06* (2006.01)

(56) References Cited

U.S. PATENT DOCUMENTS

2008/0307886 A1* 12/2008 Marsh .................. G01N 29/223
73/601

2013/0018525 A1   1/2013 Jang et al.
2013/0237811 A1* 9/2013 Mihailescu ............ A61B 5/064
600/424

OTHER PUBLICATIONS

How It Works (Scan), Parts 1-4, University of Michigan 3D Lab from http://www.um3d.dc.umich.edu/portfolio/how-it-works-scan, downloaded Jan. 29, 2014.

* cited by examiner

METHODS AND SYSTEMS FOR NON-DESTRUCTIVE INSPECTION

RELATED APPLICATION

This application claims priority under 35 U.S.C. §119(e) to U.S. Provisional Patent Application No. 61/900,239, which was filed Nov. 5, 2013, and the complete disclosure of which is incorporated herein by reference for all purposes.

FIELD

The present disclosure relates to methods and systems for non-destructive inspection.

BACKGROUND

Non-destructive inspection includes a wide group of analysis techniques used in science and industry to evaluate the properties of a test structure (e.g., one or more of a material, a part, a component, a product, and/or an apparatus) without causing damage. Such techniques may be used for quality inspection, product evaluation, product development, and maintenance inspection, in particular in industries demanding high uptime and high reliability structures. For example, aerospace test structures may be subject to non-destructive inspection at the point of manufacture and during routine operation intervals. Other industries using non-destructive inspection include health care, petrochemical, power generation, and automotive industries.

Non-destructive inspection may employ a probe including an electronic emitter and/or an electronic sensor. For example, ultrasonic inspection may use an ultrasonic transducer that emits a short-duration pulse of sound and that detects returning echoes. As another example, eddy current inspection may use an inductive probe whose impedance is affected by nearby conductive materials. The typical eddy current probe emits an electromagnetic waveform and senses a distortion in the waveform. Other types of non-destructive inspection techniques include microwave and terahertz inspection (which respectively use microwave and terahertz-wave electromagnetic radiation to interrogate the state of a test structure). Probes for non-destructive inspection may be small enough to be portable and/or to be hand-held.

One problem with non-destructive techniques is that probes typically do not intrinsically know or record their location relative to the test structure. A test structure may be a fairly large structure, potentially with complicated surface geometry. As a probe passes over a region of interest to collect test data relating to that location of the test structure, the precise location of the probe is typically neither known nor repeatable.

Non-destructive inspection systems that can track the location of the probe relative to the test structure typically use a scan bridge or similar positioning device (e.g., an x-y gantry, and/or an R-theta arm) to establish the location of an attached probe. The positioning device generally is configured to move the attached probe to a known location or to record the position of the attached probe. The inclusion of a positioning device with a non-destructive inspection system results in additional equipment to store, carry, assemble, and/or calibrate. The added complexity of operating a non-destructive inspection system with a positioning device is a burden that limits the utility of such non-destructive inspection systems, for example, in field service. Hence, there is a need for non-destructive systems that are capable of tracking the probe position without the complexity of a positioning device.

SUMMARY

Methods and systems for non-destructive inspection are disclosed. Non-destructive inspection methods comprise non-contact determination of the location of a non-destructive inspection probe, acquisition, with the probe, of test data relating to a test structure, and identification of the location on the test structure where the test data is acquired. Determination may include non-contact capturing the position of the probe and the position of the test structure with one or more electronic cameras. Determination may include generating a location data stream including probe location information derived from the captured positions of the probe and the test structure.

Acquisition, with the probe, may include placing the probe into position to acquire test data relating to at least a portion of the test structure and acquiring the test data. The acquisition may include performing electromagnetic inspection, radiative inspection, sonic inspection, and/or ultrasonic inspection. The acquisition may include generating a test data stream including test data acquired by the probe at various locations on the test structure and/or at various times.

Identification of the location on the test structure where test data is acquired may include associating the test data, and/or the test data stream, with the location of the probe relative to the test structure (probe location information), and/or the location data stream. The identification may include correlating the test data, and/or the test data stream, with the probe location information, and/or the location data stream. The identification may include associating test data with probe location information collected at substantially the same time. The identification may include generating a combined data stream including information relating to the test data associated with the location on the test structure where the test data is acquired.

Visualization methods may comprise visualization of the test data relative to the identified location. Visualization may include visualizing the test data while viewing and/or visualizing the identified location on the test structure. For example, visualization may include visualizing the test data stream, the location data stream, and/or the combined data stream.

Non-destructive inspection systems comprise a non-destructive inspection probe, one or more electronic cameras, a computer, and a display, together configured to determine the location of the probe, to acquire test data with the probe, to identify a location on a test structure associated with the test data, and to visualize the test data in relation to the test structure. Each of the probe, the electronic camera(s), the computer, and the display independently may be hand-held and/or wearable. For example, the electronic camera(s) and the display may be incorporated into personal equipment such as glasses or goggles. The system may be configured to compensate for motion of the electronic camera relative to the probe and/or test structure while determining the location of the probe relative to the test structure. For example, the electronic camera and/or computer may be configured to identify and/or track reference indicators (such as fiducial features and/or markers) associated with the probe and/or test structure.

DESCRIPTION

In non-destructive inspection, a test structure is inspected, commonly to determine the quality of manufacture, the effect of use, and/or the effect of environmental exposure. For example, welds may be inspected to determine if the initial weld was performed satisfactorily, with the inspector looking for continuity of the weld and strength of the resulting combined part. Welds also may be inspected for wear or damage after use, wear that may require a repair or replacement.

In the aerospace industry, ultrasonic inspection and eddy current inspection are two common non-destructive inspection techniques. The inspection methods may provide information regarding physical continuity of parts connected in an assembly, physical continuity of composite systems (e.g., delamination), environmental degradation (e.g., corrosion), and (im)proper assembly (e.g., missing or present features, fasteners, welds, coatings, etc.).

Figure 1:
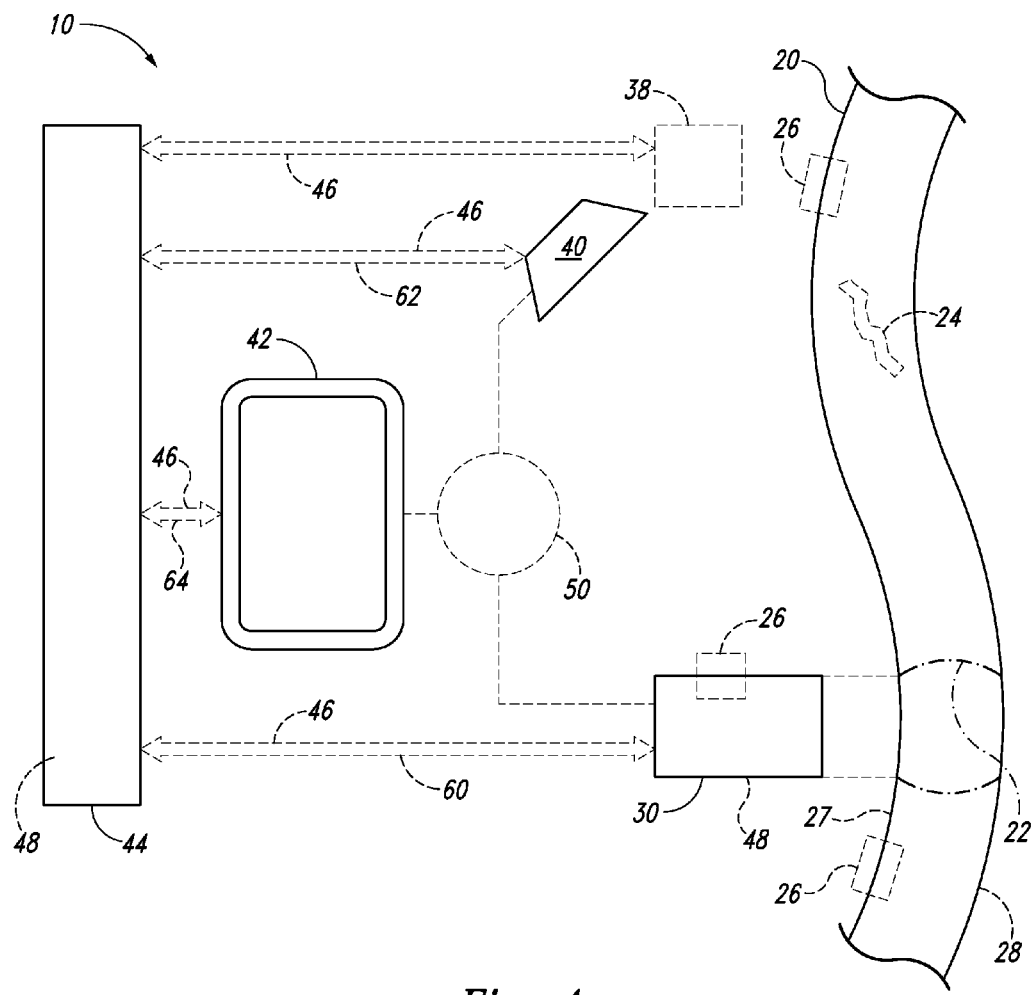
FIG. 1 is a schematic representation of a non-destructive inspection system according to the present disclosure.

FIG. 1 schematically represents a system 10 for non-destructive inspection, comprising a test structure 20 to be inspected, a probe 30 to acquire test data relating to the test structure 20 (sometimes referred to as interrogating, or probing, the test structure 20), at least one electronic camera 40 to determine the location of the probe 30 relative to the test structure 20, and a computer 44 to coordinate, and/or to control, the system 10 and to associate the test data and the location of the probe 30 relative to the test structure 20. The system 10 may be configured for a variety of non-destructive inspection modes, including electromagnetic (e.g., conductivity and/or eddy current propagation), radiative (e.g., heat emission, microwave transmission, and/or terahertz transmission), sonic (e.g., acoustic resonance, and/or acoustic reflection), and/or ultrasonic (e.g., ultrasonic refraction, ultrasonic scattering, and/or ultrasonic impedance). The system 10 may be configured to acquire test data in reflection mode (energy used to interrogate the test structure 20 is applied and sensed from the same side of the test structure 20) and/or transmission mode (energy used to interrogate the test structure 20 is applied and sensed from different sides of the test structure 20).

Test structures 20 are typically one or more of a material, a part, a component, a product, and/or an apparatus. Test structures 20 may be relatively large structures, e.g., larger than 10 cm, larger than 100 cm, or larger than 1,000 cm, and/or may be a component of a larger structure such as an at least partially assembled apparatus. For example, in the aerospace industry, test structures 20 may be an at least partially assembled aerospace vehicle or some component thereof (e.g., an aircraft, a fuselage, a wing, a frame member, or a fastener). Test structures 20 may include one or more of a metal, a polymer, a composite, a ceramic, a glass, and/or a crystal.

Further, test structures 20, especially when part of a larger assembly, may have relatively accessible surfaces, e.g., an exposed surface 27, and relatively inaccessible surfaces, e.g., a hidden surface 28. Non-destructive inspection is generally more convenient when performed from the accessible surfaces of the test structure 20 rather than the inaccessible surfaces of the test structure 20. Hence, systems 10 may be configured to interrogate the test structure 20 primarily from an exposed surface 27. For example the system 10 may be configured to interrogate the exposed surface 27, collecting information regarding the test structure 20 (regarding the exposed surface 27, the subsurface, and/or surfaces generally opposed to the exposed surface 27), without requiring further inspection from the perspective of a hidden, or generally inaccessible, surface 28.

Systems 10 may be configured to measure properties of the test structure 20 at the surface of the test structure 20, often the surface most proximate to the inspection system, and may be configured to measure surface and/or subsurface test structure properties. Subsurface properties may relate to properties of the test structure 20 that are near the surface under interrogation or beneath the surface, within the test structure 20. Systems 10 may be configured to measure surface properties of an inaccessible and/or a hidden surface 28 even though the system is interrogating the test structure 20 from an accessible, exposed surface 27.

Systems 10 may be used to identify and/or to characterize the test structure 20 at a region of interest 22. The region of interest 22 may be a region proximate to the probe 30 or may be a region identified by other techniques. For example, the region of interest 22 may be a region near a vital component and/or a feature of the test structure (e.g., a weld, a fastener, a bend, and/or an edge). Additionally or alternatively, the region of interest 22 may be located proximate to a suspected or known anomaly 24 of the test structure. An anomaly 24 may be located at least partially on the surface of the test structure 20 and may be located entirely within the test structure 20 (e.g., a surface anomaly and/or a subsurface anomaly). The anomaly 24 may be a region of different, optionally significantly different, physical properties than neighboring regions within the test structure 20. For example, an anomaly 24 may be a layer of a chemical coating, a region that lacks a coating, a region including cracks, and/or a region including corrosion products. The system 10 may be configured to search, and/or the non-destructive inspection process may encompass a search, for anomalies 24 in the test structure 20 and/or for anomalies 24 that indicate further inspection, repair, and/or replacement.

Probes 30 for systems 10 are generally non-destructive inspection probes and may be configured to non-destructively acquire test data relating to at least a portion of the test structure 20. The acquired test data principally includes data relating to the presence of a physical property and/or the magnitude of a physical property. Physical properties generally are localized properties and may relate to the surface and/or the subsurface of the test structure 20. For example, properties may relate to the location, size, shape, and/or orientation of an anomaly 24 within the test structure 20. Further, properties may indicate at least one of a defect, a fault, corrosion, wear, and damage. Illustrative, non-exclusive example properties are thickness, physical continuity, physical composition, electrical conductivity, magnetic permeability, and a physical characteristic. For example, probes 30 may include an electrical current sensor, an electrical voltage sensor, an eddy current sensor, a sonic transducer, and/or an ultrasonic transducer.

Probes 30 may include one or more energy emitters and/or one or more energy receivers. For example, a probe 30 may include an energy emitter and an energy receiver. As another example, a probe 30 may include an energy emitter and no energy receivers, or vice versa. Probes 30 may be configured to interrogate a test structure 20 in reflection mode and/or in transmission mode.

Probes 30 may be configured to collect data when in contact with the test structure 20 and/or may collect data when spaced away from the test structure 20. In FIG. 1, the probe 30 is illustrated as spaced away from the surface of the test structure 20 (in solid line) and optionally in contact with the test structure 20 (in dashed line). Non-contact sensing by the probe 30 of data throughout the test structure 20 may ease the collection of data and may avoid marring or otherwise affecting the surface of the test structure 20. Contact sensing may include close contact of a portion of the probe 30 and the surface of the test structure and/or may include a coupling medium between a portion of the probe 30 and the test structure 20. For example, ultrasonic inspection probes commonly operate better, and/or are configured to operate, with an index matching gel between the inspection probe and the surface of the test structure. As another example, an eddy current probe may directly contact the surface of the test structure.

Probes 30 may be configured to be operated directly by an operator 50. For example, a probe 30 may be a hand-held probe 30 and/or may include a handle to aid the operator 50 in manipulating the position of the probe 30 relative to the test structure 20. The probe 30 may be configured to be primarily supported by the operator 50 during data acquisition, lacking any scan bridge, gantry, or support arm.

Probes 30 may be configured to collect data from a single location and/or from a series of locations. A series of locations may be essentially one-dimensional, e.g., a line scan along an interrogation line on the surface of the test structure 20, or may be essentially two-dimensional, e.g., an area scan of the surface of the test structure 20. Probes 30, and/or systems 10, may be configured to collect data from a series of locations essentially simultaneously and/or substantially simultaneously. Probes 30 may be configured to collect data from a series of locations with or without movement of the probe 30 (e.g., using an array of emitters and/or receivers such as a phased array of ultrasonic transducers, or a focal plane array).

Probes 30 and/or systems 10 may be configured to collect test data in several different modes. For example, a common scan mode is called an A-scan. An A-scan includes data relating to a single location of the test structure 20 and a property (e.g., the magnitude of a probed property and/or the depth of a probed property) at the location on the test structure 20. As another example, the probe 30 and/or the system 10 may be configured to collect a B-scan. A B-scan is typically a group of data relating to a (typically linear) series of locations. The data may indicate a property of the test structure 20 along an interrogation line on the surface of the test structure 20 (e.g., a single surface dimension). B-scans commonly are presented as two-dimensional cross-sectional views of the test structure 20 along the interrogation line, with one direction a surface distance and the other direction a depth. Properties of the test structure 20 within the cross section may be indicated by shading and/or false color. As another example, probes 30 and/or systems 10 may be configured to collect C-scan data. A C-scan typically is a two-dimensional scan of the surface of the test structure where the data additionally relates to properties of the test structure on and under the interrogated surface. Typically, a C-scan does not indicate the depth of a property (though the property may be related to depth, e.g., thickness). However, the probe 30 and/or system 10 may be configured to collect data at a particular depth below the interrogated surface. C-scans typically are presented as two-dimensional (plan projection) images, with the properties visualized by shading and/or false color. As an additional example, probes 30 and/or systems 10 may be configured to collect data in a D-scan format. A D-scan includes a three-dimensional collection of data relating to the properties of the test structure 20, including the projected surface location and the depth of the property. Typically, a D-scan is visualized with a three-dimensional visualization (e.g., one or more two-dimensional projections of the data and/or a three-dimensional image), with the property indicated by shading and/or false color.

Probes 30 may be configured to transmit raw data from the interrogation of the test structure 20. Additionally or alternatively, probes 30 may be configured to preprocess raw data to result in derived data relating to more physically relevant properties of the test structure 20. Probes 30 may generate and/or transmit a test data stream 60 that includes data related to one or more properties of the test structure 20. For example, probes 30 may be configured to transmit data relating to the test structure 20 for each location interrogated. As another example, probes 30 may be configured to transmit data relating to the region of interest 22, an anomaly 24, and/or the region of the test structure 20 proximate to the probe 30, as the data is collected. Probes 30 may include data storage devices (e.g., a computer readable medium 48) to retain the test data. Probes 30 may include a computer processor to calculate derived data and/or parameters relating to the raw data.

Systems 10 may comprise a plurality of probes 30 with each probe 30 independently configured to acquire test data relating to the test structure 20. The systems 10 and/or the probes 30 may be configured such that at least two probes 30 may be operated at least partially concurrently and/or at least partially sequentially. Systems 10 may be configured to independently capture the position of each probe 30 and independently determine the location of each probe 30 relative to the test structure 20.

Systems 10 include at least one electronic camera 40 to determine the location of the probe 30 relative to the test structure 20. The location may include the relative displacement and orientation of the probe 30 and the test structure 20. The one or more electronic cameras 40 are configured to capture the position of the probe 30 and the position of the test structure 20 by non-contact imaging (i.e., capturing does not require direct physical contact or other potentially interfering interactions). The position may include the displacement and orientation of at least a portion of the object with respect to the electronic camera field of view and/or other objects within the electronic camera field of view. The system 10 may be configured to capture the position of the probe 30 and the test structure 20 at least partially concurrently and/or at least partially sequentially. Generally, systems 10 are configured to determine the location of the probe 30 relative to the test structure 20 by comparing the captured position of the probe 30 and the captured position of the test structure 20.

Systems 10 may be configured to vary the position (including the orientation) of the electronic camera 40 while determining the location of the probe 30 relative to the test structure 20. Additionally or alternatively, systems 10 may be configured to determine the location of the probe 30 relative to the test structure 20 despite, or with the aid of, changes in the position (including the orientation) of the electronic camera 40. For example, the electronic camera 40 may be a hand-held camera or may be configured to be worn and/or carried by the operator 50 during operation of the system 10 (i.e., the operator 50 is the primary support of the electronic camera 40, with no tripod, gantry, or other support required). The system 10 may be configured to track the position of the probe 30 and the position of the test structure 20 while the electronic camera 40 is moved by the operator 50. An electronic camera 40 may be configured to be worn by the operator 50. For example, the electronic camera 40 may be generally attached to the operator 50 (worn on and/or associated with a body part such as the head, arm, shoulder, and hand), incorporated into clothing, and/or incorporated into personal equipment (e.g., a hat, glasses, goggles, a headband, an armband, a wristband, a chest band, a lanyard, a harness, a sleeve, a cuff, and a belt).

Where the system 10 comprises one electronic camera 40, that electronic camera 40 is configured to capture the position of the probe 30 and the position of the test structure 20. Where the system 10 comprises a plurality of electronic cameras 40, each electronic camera 40 may be configured to capture the position of the probe 30 and/or the position of the test structure 20, at least when the probe 30 and/or the test structure 20, respectively, is within the field of view of that electronic camera 40. For example, one of the plurality of electronic cameras 40 may be configured to capture the positions of both the probe 30 and the test structure 20. As another example, one electronic camera 40 may be configured to capture the position of the probe 30 and another electronic camera 40 may be configured to capture the position of the test structure 20.

Plural electronic cameras 40 may provide multiple points of view of the probe 30 and/or the test structure 20. Multiple points of view may be used to more fully observe the probe 30 and/or the test structure 20, for example to eliminate and/or diminish the effects of any hidden zones in the system 10, or, as another example, to expand the total observed zone of the system 10. Additionally or alternatively, multiple points of view may be used for various types of three-dimensional imaging such as stereo-imaging and/or photogrammetry.

The captured position of the probe 30 and/or the captured position of the test structure 20 may be a two-dimensional position (as examples, a position within a plane and a position on the surface of the test structure 20) or may be a three-dimensional position. An electronic camera 40 may capture a two-dimensional image and/or a three-dimensional image of a portion of the system 10. A two-dimensional position may be derived directly from a two-dimensional image or may be calculated by capturing a series of two-dimensional images (e.g., at a series of times, under different lighting conditions, under different system conditions, as objects in the images are moving, and/or with different electronic cameras 40). A two-dimensional position may be derived from a projection of a three-dimensional image or a series of three-dimensional images. A three-dimensional position may be derived directly from a three-dimensional image or may be calculated by capturing a series of two-dimensional and/or three-dimensional images. For example, photogrammetry may be used to calculate the three-dimensional position of an object using a series of images of the object. Photogrammetry may use images from a single electronic camera 40 captured at different times and/or under different conditions, and/or may use images from multiple electronic cameras 40 with different points of view.

The electronic camera(s) 40 of systems 10 are configured to capture the position of the probe 30 and/or the position of the test structure 20 by collecting an image of electromagnetic radiation propagating to and/or from the probe 30 and the test structure 20, respectively. The electronic camera 40 may be a camera configured to detect light (visible light, infrared light, near-infrared light, and/or ultraviolet light), and/or thermal energy.

Electronic cameras 40 may be configured to capture an image upon a trigger (e.g., an electronic signal generated by actions of the operator 50, optionally present near the test structure 20, and/or an electronic signal generated by automated control systems). The trigger may be a periodic trigger and/or may be related to the presence and/or movement of a component of the system 10. For example, the operator may trigger the capture of an image, and ultimately the capture of a position, before, during, and/or after acquiring, with the probe 30, test data related to the test structure 20. As another example, the system 10 may be configured to capture an image, and ultimately to capture a position, before, during, and/or after acquiring, with the probe 30, test data related to the test structure 20.

Electronic cameras 40 may be configured to capture a series of images, for example, a quasi-continuous series of images at a regular time interval. An electronic camera 40 configured to capture a time series of images at a rate similar to or faster than the rate of human perception may be referred to as a video camera. An electronic camera 40 may capture images at a frame rate of greater than 1 fps (frames per second), greater than 2 fps, greater than 3 fps, greater than 4 fps, greater than 6 fps, greater than 8 fps, greater than 10 fps, greater than 12 fps, greater than 15 fps, greater than 18 fps, greater than 20 fps, greater than 24 fps, greater than 30 fps, greater than 60 fps, greater than 100 fps, greater than 1000 fps, about 3 fps, about 12 fps, about 15 fps, about 24 fps, about 30 fps, about 60 fps, about 72 fps, 1-100 fps, and/or 1-60 fps. Other frame rates within these ranges, as well as frame rates outside of these ranges, also are within the scope of the present disclosure.

Electronic cameras 40 and/or systems 10 may be configured to determine the position of the probe 30 and/or the test structure 20 with accuracy and/or reproducibility. The accuracy and/or reproducibility of the determination may be influenced by many factors such as motion while capturing images (motion of the electronic camera 40, motion of the probe 30, and/or motion of the test structure 20), exposure (amount of electromagnetic radiation collected), optics (e.g., resolving power, focus, field of view), and contrast within the scene imaged. For example, a compact HD video camera may resolve physical features of about 1 mm at a distance of 0.5-1 m.

Electronic cameras 40 may be configured to transmit raw data from the capture of the position of the probe 30 and/or the position of the test structure 20. Additionally or alternatively, electronic cameras 40 may be configured to preprocess raw data to result in derived data relating more directly to the position of the probe 30, the position of the test structure 20, and/or the location of the probe 30 relative to the test structure 20. Electronic cameras 40 may generate and/or transmit a location data stream 62 that includes data related to the location of the probe 30 relative to the test structure 20, the position of the probe 30, and/or the position of the test structure 20. For example, electronic cameras 40 may be configured to transmit a location data stream 62 in the form of a video image stream.

Systems 10 may comprise an illuminator 38 to illuminate at least one of the probe 30 and/or the test structure 20. Additionally or alternatively, systems 10 may be configured to use ambient illumination. An illuminator 38 may be a source of electromagnetic radiation that may be detected by the electronic camera 40, generally light, and thus the illuminator 38 may be a light source. The illuminator 38 may be configured to aid capturing the position of the probe 30 and/or the position of the test structure 20. For example, the illuminator 38 may provide sufficient light for the electronic camera 40 to capture a useable image. The illuminator 38 may be configured to eliminate shadows and/or substantially uniformly illuminate the probe 30 and/or the test structure 20. The illuminator 38 may be configured to project spatially structured and/or temporally structured energy (e.g., light) onto at least one of the probe 30 and the test structure 20. With spatially structured light, structured illumination techniques may be used to capture and/or determine the position of the probe 30 and/or the test structure 20. Generally, structured illumination techniques rely on imaging distortions of spatially structured illumination caused by the viewing direction and the shape of the object illuminated. Structured illumination techniques may yield a three dimensional position of the surface of an illuminated object. With temporally structured light, the illumination may be synchronized with the imaging of the electronic camera 40 (e.g., a flash and/or a strobe). Further, temporally structured light may be used to indicate the desired moment to capture an image. For example, a strobe may effectively restrict imaging to times when the strobe is active. As another example, the illuminator 38 may emit a beacon signal, imparting a distinguishable feature in images captured during the beacon emission.

Systems 10 may comprise one or more reference indicators 26—indicators on, in, and/or associated with, a known position (possibly including a known orientation) of an object that may be used to identify the position (possibly including the orientation) of the object. For example, the test structure 20 and the probe 30 each independently may include a reference indicator 26. Reference indicators 26 may be configured to aid identification, location, and/or tracking of the probe 30 and/or the test structure 20. The electronic camera 40 may capture an image of one or more reference indicators 26 on and/or associated with the probe 30 and/or the test structure 20. The electronic camera 40 and/or the system 10 may be configured to determine the position (possibly including the orientation) of any reference indicators 26 within an image and to use the determined position of one or more reference indicators 26 as a proxy for, or to calculate, the position of the probe 30, the position of the test structure 20, and/or the location of the probe 30 relative to the test structure 20. Multiple reference indicators 26 may be used for redundancy and/or robustness of the determination process. For example, the test structure 20 may include more than one reference indicator 26 so that if one fails or falls outside the field of view of the electronic camera 40, at least one other reference indicator 26 may positively indicate the position of the test structure 20.

A reference indicator 26 may be one or more of a fiducial feature and a marker. A fiducial feature is a distinguishable feature of an object that may be used to identify the object and/or the object's position. A marker is a distinguishable element added to and/or integrated into an object at a known position on the object. A marker may distinctively label the object and/or the object's position. A marker may be associated with, and/or located on, an identifiable feature, a reference point, and/or a fiducial feature of an object.

Reference indicators 26 may each be unique. Reference indicators 26 on the probe 30 may be different than reference indicators 26 on the test structure 20. Reference indicators 26 may include optical and/or electronic identification. Reference indicators 26 may include passive and/or active elements. A passive element does not emit its own energy, nor does it specifically respond to incoming energy. Illustrative, non-exclusive example passive elements include reflective elements, resistive elements, inductive elements, fluorescent elements, luminescent elements, and colored elements. A passive element may incorporate a distinctive color and/or symbol. An active element may emit energy and/or may specifically respond to an incoming signal. Illustrative, non-exclusive example active elements include a light source, an RFID (radio-frequency identification) tag, an electronic emitter, a photodetector, and an electronic receiver.

Systems 10 may comprise a display 42 to visualize test data relating to the test structure 20 acquired by the probe 30 (i.e., data relating to a physical property of the test structure 20).

The display 42 may be configured to visualize the test data in relation to the test structure 20, and may be configured to visualize the test data in relation to the location on the test structure 20 where the test data was acquired. For example, the display 42 may be configured to display the test data while allowing the operator 50 to view the corresponding portion of the test structure 20. As another example, display 42 may be configured to display the test data in conjunction with one or more images and/or renderings representing the corresponding portion of the test structure 20. Generally, the display 42 is configured to display a combined data stream 64 including data related to the test data acquired by the probe 30 and the relative location of the probe 30 while the test data is acquired. The combined data stream 64 is the result of the association of the test data stream 60 (the data stream of the test data acquired by the probe 30) and the location data stream 62 (the data stream related to the location of the probe 30 relative to the test structure 20).

The display 42 and/or the system 10 may be configured to merge the test data and the relative location of the probe 30. The merging and/or visualizing may be at least partially concurrent with the acquisition of the test data with the probe 30. The display 42 and/or the system 10 may be configured to blend an image derived from the test data and an image of the relative location of the probe 30 when the test data was acquired. The image of the relative location of the probe 30 may be part of a video stream of the relative location of the probe 30.

The display 42 may include a head-up display, sometimes referred to as a heads-up display, a head-mounted display (e.g., incorporated into glasses or goggles), and/or a display worn by the operator 50. A head-up display is a type of display configured to overlay data onto a scene. It typically includes a generally transparent element (e.g., a beamsplitter, a transparent screen) where data may be viewed while allowing a user to see through the transparent element to the scene beyond (e.g., the environment). A head-mounted display and/or a user-worn display may be a head-up display or may be an electronic display that does not include transparent elements.

The display 42 may be a portable and/or a hand-held display or may be configured to be worn and/or carried by the operator 50 during operation of the system 10 (i.e., the operator 50 is the primary support of the display 42, with no tripod, gantry, or other support required).

The display 42 may be configured to receive data relating to the test data acquired by the probe 30 and position data captured by the electronic camera 40, for example at least a portion of the combined data stream 64.

Systems 10 may comprise a computer 44 (a computing device) configured to determine a location of the probe 30 relative to the test structure 20 based upon the captured position of the probe 30 and the captured position of the test structure 20, to acquire the test data from the probe 30, and/or to identify a location on the test structure 20 where the test data is acquired by associating the acquired test data and the location of the probe 30 relative to the test structure 20. For example, the computer 44 may be configured to calculate the location of the probe 30 relative to the test structure 20 based upon data relating to the position of the probe 30 and to the position of the test structure 20. As another example, the computer 44 may be configured to associate the location of the probe 30 relative to the test structure 20 with the test data acquired at that location. Where more than one test data set is acquired at substantially the same location on the test structure 20 (e.g., with more than one probe 30, or repeated test data sets from the same probe 30), the test data sets acquired at substantially the same location may be associated and may be collectively or individually associated with the location on the test structure 20.

The computer 44 may be configured to determine the location of the probe(s) 30 and to acquire the test data from the probe(s) 30 in essentially any order. For example, the computer may be configured to determine the location of the probe 30 at least partially concurrently and/or at least partially sequentially with the acquisition of test data. The computer 44 may be configured to acquire test data, to capture position of the probe 30, and to capture position of the test structure 20 essentially continuously, optionally recording the time of the acquisition and capturing. The computer 44 may be configured to acquire test data when the probe 30 reaches a suitable, and/or predetermined, position (e.g., a region of interest 22). The computer 44 may be configured to capture the position of the probe 30 and/or the position of the test structure 20 at the beginning of test data acquisition, during test data acquisition, and/or after successful test data acquisition.

Generally, the computer 44 may be configured to coordinate and/or control the system 10. For example, the computer 44 may control the acquisition of test data with the probe 30, and may control the capture of the position of the probe 30 and the capture of the position of the test structure 20 with the electronic camera 40 (and the optional illuminator 38). The computer 44 may control the display 42. The computer 44 may be in electronic communication via a communication link 46 with one or more of the probe 30, the electronic camera 40, the illuminator 38, and the display 42. Any communication link 46, when present, may be a wireless link operating with one or more wireless protocols such as BLUETOOTH protocol and WI-FI protocol (e.g., compliant with IEEE 802.11 standards).

Though the computer 44 may control the system 10 generally, the operator 50 may have ultimate control of the system 10. For example, the operator 50 may initiate the acquisition of test data with the probe 30 and may choose the location of probe 30 during test data acquisition.

The computer 44 may be configured to associate test data (e.g., the test data stream 60) and the probe location information (e.g., the location data stream 62) to identify a location with particular test data (e.g., creating the combined data stream 64). The computer 44 may be configured to associate test data acquired at a plurality of probe locations with the plurality of probe locations. The location of the probe 30 may be associated with the test data acquired at that location by correlating the test data (and/or the test data stream 60) with the probe location information (and/or the location data stream 62). The correlation may include a mathematical correlation of the test data stream 60 and the location data stream 62. The correlation may include a comparison of the test data and the probe location information. The test data and the probe location information may be associated if the test data and the probe location information are acquired substantially simultaneously. For example, the test data may be acquired by the probe 30 at least partially concurrently with the determination of the location of the probe 30 from the position of the probe 30 and the position of the test structure 20 captured by the electronic camera 40. Test data and probe location information may be associated if the test data and the probe location information each include a time stamp, i.e., a record of the time the data was recorded (e.g., when the test data was acquired and when the probe location information was determined). Test data and the probe location information recorded at substantially the same time may be associated.

The computer 44 may be a portable computer, a wearable computer, a hand-held computer, and/or a mobile computing device. The computer 44 may include a computer readable medium 48 (e.g. a memory device) that includes computer-executable instructions that, when executed, allow the computer to perform one or more of the functions described above and/or the methods described below. A computer readable medium 48 is any medium readable by a computer. It typically includes a medium that is configured to store computer instructions, i.e., a computer readable storage medium (e.g., a hard drive, flash memory, RAM), and does not include transitory, propagating electrical or electromagnetic signals per se. Hence, a computer readable medium 48 is non-transitory and may be referred to as a non-transitory computer readable medium.

Systems 10 may comprise an apparatus that includes two or more components, e.g., a single apparatus may include two or more probes 30, electronic cameras 40, computers 44, illuminators 38, and/or displays 42. For example, a computer 44, a display 42, and an electronic camera 40 may be combined in one apparatus.

Figure 2:
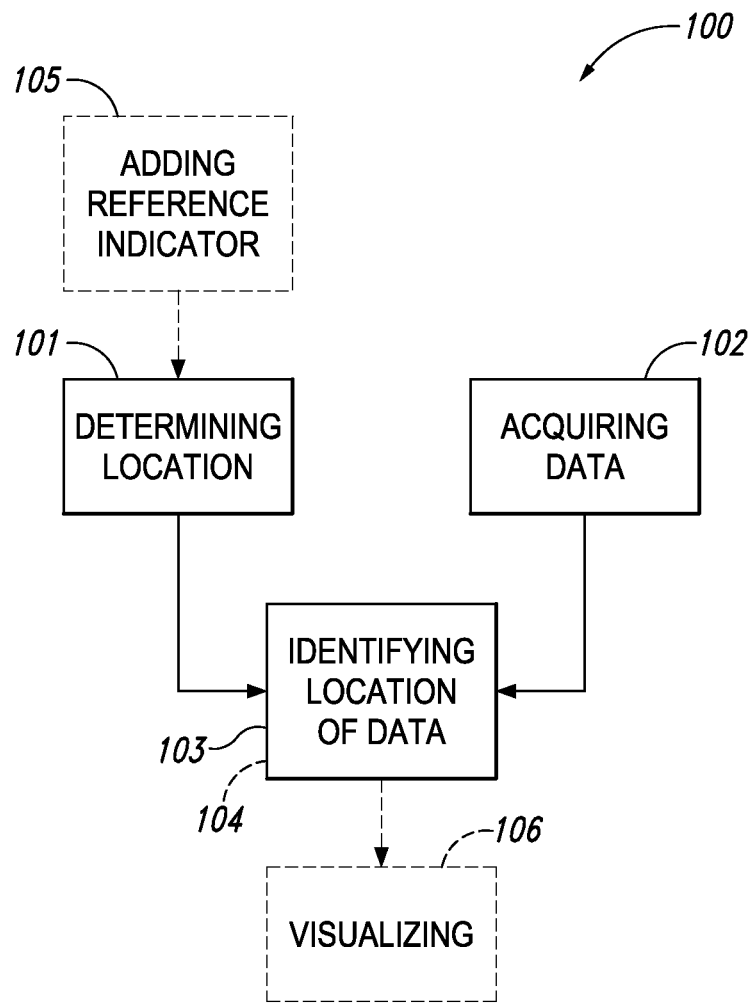
FIG. 2 is a flowchart of methods of non-destructive inspection according to the present disclosure.

FIG. 2 is a flowchart of methods 100 of non-destructive inspection. Methods 100 comprise determining 101 a location of a probe 30 relative to a test structure 20, acquiring 102, with the probe 30, test data relating to the test structure 20, and identifying 103 a location on the test structure 20 where the test data is acquired by associating 104 the test data and the location of the probe 30 relative to the test structure. The determining 101 includes non-contact capturing of a position of the probe 30 and non-contact capturing of a position of the test structure 20. The determining 101 (including the capturing of the position of the probe 30 and the capturing of the position of the test structure 20) is a non-contact operation, i.e., requiring no direct mechanical contact between the probe 30 and the device capturing the position of the probe 30, and requiring no direct mechanical contact between the test structure 20 and the device capturing the position of the test structure 20. Non-contact capturing may include using an electronic camera 40 to capture images of the probe 30 and/or the test structure 20.

The determining 101 may be performed at essentially any time relative to the acquiring 102, e.g., at least partially concurrently and/or at least partially sequentially. For example, the determining 101 and the acquiring 102 may be essentially continuous processes. As another example, the determining 101, or at least one of the capturing the position of the probe 30 and the capturing of the position of the test structure 20, may be essentially continuous while the acquiring 102 is essentially discontinuous. The determining 101 may trigger the start of the acquiring 102 and/or vice versa. For example, the acquiring 102 may be triggered by the identification of a suitable, and/or predetermined, location by the determining 101. As another example, the determining 101 may be initiated before, during, or after the acquiring 102 (e.g., the determining 101 may be initiated after the successful acquiring 102).

The determining 101 may include capturing the position of the probe 30 and capturing the position of the test structure 20 in essentially in any order, e.g., at least partially concurrently and/or at least partially sequentially. Each of the capturing of the position of the probe 30 and the capturing of the position of the test structure 20 independently may be an essentially continuous or discontinuous process.

The determining 101 may include generating a location data stream 62 including data relating to the location of the probe 30 relative to the test structure 20, the captured position of the probe 30, and/or the captured position of the test structure 20. The determining 101 may include recording the time the position of the probe 30 was captured, the time the position of the test structure 20 was captured, and/or the time the location of the probe 30 relative to the test structure 20 was determined.

The determining 101 may include using an electronic camera 40, optionally to capture the position of the probe 30 and/or the position of the test structure 20. Additionally or alternatively, capturing the position of the probe 30 and/or capturing the position of the test structure 20 may include calculating the respective position(s) based upon one or more images captured with the electronic camera 40. The determining 101 may include varying the location of the electronic camera 40 with respect to the test structure 20 and/or the probe 30. The determining 101 may include compensating for variations in the location of the electronic camera 40 with respect to the test structure 20 and/or the probe 30.

The determining 101 may include capturing a two-dimensional or a three-dimensional position of the probe 30 and/or the test structure 20. The determining 101 may include imaging with the electronic camera 40, video imaging with the electronic camera 40, using stereo-imaging, and/or using photogrammetry. The determining 101 may include using a plurality of electronic cameras 40, as examples, using at least a pair of electronic cameras 40 for stereo-imaging, and using one electronic camera 40 to capture the position of the probe 30 while using at least one other electronic camera 40 to capture the position of the test structure 20. Additionally or alternatively, using a plurality of electronic cameras 40 may diminish the effects of hidden zones and/or increase the total field of view relative to using a single electronic camera 40. Using an electronic camera 40 may include wearing the electronic camera 40 and/or hand-holding the electronic camera 40 (e.g., the operator 50 is the primary support for the electronic camera 40, with no tripod, gantry, or other support required).

The determining 101 may include illuminating at least one of the probe 30 and the test structure 20. Illuminating may include using ambient light, using an illuminator 38 (e.g., a light source), projecting spatially structured light, and/or projecting temporally structured light. With spatially structured light, the determining 101 may include measuring distortions of the spatially structured light caused by the probe 30 and/or the test structure 20 to determine a three-dimensional location of the probe 30 relative to the test structure 20. With temporally structured light, the determining 101 may include flashing and/or strobing the illumination.

The determining 101 may include identifying one or more reference indicators 26 of at least one of the probe 30 and the test structure 20. Further, the determining 101 may include tracking one or more reference indicators 26. The reference indicator 26 may be identified by a passive response to incoming energy. For example, the reference indicator 26 may be identified by reflection, fluorescence, luminescence, color, shape, and/or symbol. The reference indicator 26 may be identified by an active transmission from the reference indicator 26. For example, the reference indicator 26 may include an active element.

Methods 100 may comprise adding 105 reference indicators 26 (e.g., markers) to the test structure 20 and/or the probe 30 to aid tracking of the test structure 20 and/or the probe 30. The adding 105 may include associating a marker with one or more of an identifiable feature, a reference point, and a fiducial feature of the test structure 20 and/or the probe 30.

Methods 100 comprise acquiring 102 non-destructive test data relating to the test structure 20. The acquiring 102 may include performing a reflection mode measurement and/or a transmission mode measurement. The acquiring 102 may include acquiring test data relating to a region of interest 22, an anomaly 24, a surface property, and/or a subsurface property of the test structure 20. The acquiring 102 may include performing an A-scan, a B-scan, a C-scan, and/or a D-scan. The acquiring 102 may include generating a test data stream 60 of data relating to the test data acquired and/or recording the time the test data was acquired.

The acquiring 102 may include performing a contact and/or a non-contact measurement with the probe 30. The acquiring 102 may include hand-holding the probe 30 (e.g., the operator 50 providing the primary support, with no scan bridge, gantry, support arm, or other support required).

Methods 100 comprise identifying 103 the location on the test structure 20 where the test data is acquired by associating 104 the test data and the location of the probe 30. The associating 104 may include associating the test data stream 60 with the location data stream 62 to generate a combined data stream 64. Generally, the test data stream 60 includes test data acquired from different locations on the test structure 20 (a plurality of locations), possibly including test data from a region of interest 22 (e.g., an anomaly 24). Generally, the location data stream 62 includes probe location information (a plurality of probe locations) determined from different positions of the probe 30 and the test structure 20, without any direct relation to the test data acquired.

The associating 104 may include correlating the location of the probe 30, and/or the location data stream 62, with the test data acquired at that location, and/or with the test data stream 60. The correlation may include a mathematical correlation of the test data stream 60 and the location data stream 62. The correlation may include a comparison of the test data and the probe location information. The associating 104 may include associating test data and the location of the probe 30 collected and/or recorded at substantially the same time (e.g., substantially simultaneously).

Methods 100 may comprise visualizing 106 the test data, acquired with the probe 30, in relation to the test structure 20. The visualizing 106 may be performed at least partially concurrently with the acquiring 102 the test data. The visualizing 106 may include merging the test data and the relative location of the probe 30. The visualizing may include blending an image derived from the test data and one or more images related to the relative location of the probe 30 (e.g., an image of the test structure 20, a rendering of the test structure 20, and/or a video stream of the test structure 20).

Methods 100 may comprise multiplexing, i.e., determining 101, acquiring 102 and identifying 103 more than once with a single probe 30 and/or with more than one probe 30. Where more than one set of test data may be associated with the same location on the test structure 20, the different test data sets may be associated with each other. Associating the different test data sets may be performed analogous to the associating 104.

Illustrative, non-exclusive examples of inventive subject matter according to the present disclosure are described in the following enumerated paragraphs:

A1. A method of non-destructive inspection of a test structure, the method comprising:

determining a location of a probe relative to the test structure, wherein the determining includes non-contact capturing of a position of the probe and non-contact capturing of a position of the test structure;

acquiring, with the probe, test data relating to the test structure; and identifying a location on the test structure where the test data is acquired by associating the test data and the location of the probe relative to the test structure.

A2. The method of paragraph A1, wherein the capturing the position of the probe and the capturing the position of the test structure are performed at least partially concurrently.

A3. The method of any of paragraphs A1-A2, wherein the capturing the position of the probe and the capturing the position of the test structure are performed at least partially sequentially.

A4. The method of any of paragraphs A1-A3, wherein the determining the location of the probe and the acquiring test data are performed at least partially concurrently.

A5. The method of any of paragraphs A1-A4, wherein the determining the location of the probe and the acquiring test data are performed at least partially sequentially.

A6. The method of any of paragraphs A1-A5, wherein the determining includes using an electronic camera to determine the relative location of the probe and the test structure.

A6.1. The method of paragraph A6, wherein a location of the electronic camera varies with respect to the probe and the test structure while determining the location of the probe, and wherein the determining includes compensating for variations in the location of the electronic camera.

A6.2. The method of any of paragraphs A6-A6.1, wherein the using the electronic camera includes capturing with the electronic camera at least one of the position of the probe and the position of the test structure.

A6.3. The method of any of paragraphs A6-A6.2, wherein the electronic camera is a video camera.

A6.4. The method of any of paragraphs A6-A6.3, wherein the using the electronic camera includes acquiring images at a frame rate of greater than 1 fps, greater than 2 fps, greater than 3 fps, greater than 4 fps, greater than 6 fps, greater than 8 fps, greater than 10 fps, greater than 12 fps, greater than 15 fps, greater than 18 fps, greater than 20 fps, greater than 24 fps, greater than 30 fps, about 3 fps, about 12 fps, about 15 fps, about 24 fps, about 30 fps, about 60 fps, and/or 1-60 fps.

A6.5. The method of any of paragraphs A6-A6.4, wherein the using the electronic camera includes capturing the position of the probe by photogrammetry, wherein the position of the probe is a three dimensional position.

A6.6. The method of any of paragraphs A6-A6.5, wherein the using the electronic camera includes capturing the position of the test structure by photogrammetry, wherein the position of the test structure is a three dimensional position.

A6.7. The method of any of paragraphs A6-A6.6, wherein the using the electronic camera includes acquiring at least one of a visible light image, an infrared image, an ultraviolet image, and a thermal image.

A6.8. The method of any of paragraphs A6-A6.7, wherein the using an electronic camera includes using a plurality of electronic cameras.

A6.8.1. The method of paragraph A6.8, wherein the using the plurality of electronic cameras includes using at least a pair of electronic cameras for stereo-imaging.

A6.8.2. The method of any of paragraphs A6.8-A6.8.1, wherein the using the plurality of electronic cameras includes using at least one electronic camera to capture the position of the probe and at least one other electronic camera to capture the position of the test structure.

A6.8.3. The method of any of paragraphs A6.8-A6.8.2, wherein the using the plurality of electronic cameras includes using the plurality of electronic cameras to diminish the effects of hidden zones.

A6.9. The method of any of paragraphs A6-A6.8.3, wherein the electronic camera is a user-worn camera, optionally a head-mounted camera.

A6.10. The method of any of paragraphs A6-A6.9, wherein the using the electronic camera includes wearing the electronic camera.

A6.11. The method of any of paragraphs A6-A6.10, wherein using the electronic camera includes hand-holding the electronic camera.

A6.12. The method of any of paragraphs A6-A6.11, wherein the determining includes illuminating at least one of the probe and the test structure.

A6.12.1. The method of paragraph A6.12, wherein the illuminating includes using ambient illumination.

A6.12.2. The method of any of paragraphs A6.12-A6.12.1, wherein the illuminating includes using an illuminator.

A6.12.3. The method of any of paragraphs A6.12-A6.12.2, wherein the illuminating includes projecting spatially structured light onto at least one of the probe and the test structure.

A6.12.3.1. The method of paragraph A6.12.3, wherein the determining includes determining the location of the probe by measuring distortions of the spatially structured light caused by the probe, wherein the location is a three dimensional location.

A6.12.3.2. The method of any of paragraphs A6.12.3-A6.12.3.1, wherein the determining includes determining the location of the test structure by measuring distortions of the spatially structured light caused by the test structure, wherein the location is a three dimensional location.

A6.12.4. The method of any of paragraphs A6.12-A6.12.3.2, wherein the illuminating includes projecting temporally structured light onto at least one of the probe and the test structure, optionally wherein the temporally structured light is flashing and/or strobing.

A7. The method of any of paragraphs A1-A6.12.4, wherein the determining the location includes identifying a reference indicator of at least one of the probe and the test structure, optionally wherein the reference indicator is at least one of a fiducial feature and a marker.

A7.1. The method of paragraph A7, wherein the reference indicator is at least partially passive.

A7.1.1. The method of paragraph A7.1, wherein the reference indicator includes a reflective element.

A7.1.2. The method of any of paragraphs A7.1-A7.1.1, wherein the reference indicator includes a distinctive color and/or symbol.

A7.2. The method of any of paragraphs A7-A7.1.2, wherein the reference indicator is at least partially active.

A7.3. The method of any of paragraphs A7-A7.2, wherein the identifying the reference indicator includes at least one of optical identification and electronic identification.

A8. The method of any of paragraphs A1-A7.3, wherein the probe includes a reference indicator to aid tracking of the probe, optionally wherein the reference indicator is at least one of a fiducial feature and a marker.

A9. The method of any of paragraphs A1-A8, further comprising: adding one or more markers to the probe to aid tracking of the probe.

A9.1. The method of paragraph A9, wherein adding includes associating a marker with one or more of an identifiable feature, a reference point, and a fiducial feature of the test structure.

A10. The method of any of paragraphs A1-A9.1, wherein the test structure includes a reference indicator to aid tracking of the test structure, optionally wherein the reference indicator is at least one of a fiducial feature and a marker.

A11. The method of any of paragraphs A1-A10, further comprising:
adding one or more markers to the test structure to aid tracking of the test structure.

A11.1. The method of paragraph A11, wherein adding includes associating a marker with one or more of an identifiable feature, a reference point, and a fiducial feature of the test structure.

A12. The method of any of paragraphs A1-A11.1, wherein the test structure is an aerospace component, optionally assembled with other components, forming at least part of an aerospace vehicle.

A13. The method of any of paragraphs A1-A12, wherein the test structure has an exposed surface and a hidden surface, and wherein the acquiring includes acquiring test data with the probe from the exposed surface.

A13.1. The method of paragraph A13, wherein the acquiring includes acquiring test data with the probe only from the exposed surface.

A13.2. The method of any of paragraphs A13-A13.1, wherein the test structure has a hidden surface, and wherein the acquiring does not include acquiring test data with the probe from the hidden surface.

A14. The method of any of paragraphs A1-A13.2, wherein the acquiring includes hand-holding the probe.

A15. The method of any of paragraphs A1-A14, wherein the probe is a hand-held probe.

A16. The method of any of paragraphs A1-A15, wherein the acquiring test data includes non-destructively measuring a property of the test structure with the probe, optionally wherein the property includes a subsurface property.

A17. The method of any of paragraphs A1-A16, wherein the probe is configured to non-destructively measure a property of the test structure, optionally wherein the property includes a subsurface property.

A17.1. The method of paragraph A17, wherein the probe includes at least one of an electrical current sensor, an electrical voltage sensor, an eddy current sensor, a sonic transducer, and an ultrasonic transducer.

A18. The method of any of paragraphs A1-A17.1, wherein the test data relating to the test structure includes at least one of electrical conductivity, magnetic permeability, physical continuity, thickness, and a physical characteristic.

A19. The method of any of paragraphs A1-A18, wherein the test data relating to the test structure indicates at least one of a defect, a fault, corrosion, wear, and damage.

A20. The method of any of paragraphs A1-A19, wherein the test data relating to the test structure indicates the location, size, shape, and/or orientation of an anomaly within the test structure.

A20.1. The method of paragraph A20, wherein the anomaly is a subsurface anomaly.

A20.2. The method of any of paragraphs A20-A20.1, wherein the anomaly is a surface anomaly.

A21. The method of any of paragraphs A1-A20.2, further comprising:
visualizing the test data in relation to the test structure.

A21.1. The method of paragraph A21, wherein the visualizing is performed at least partially concurrently with the acquiring test data.

A21.2. The method of any of paragraphs A21-A21.1, wherein the visualizing includes merging the test data and the relative location of the probe.

A21.3. The method of any of paragraphs A21-A21.2, wherein the visualizing includes blending an image derived from the test data and an image of the relative location of the probe.

A21.4. The method of any of paragraphs A21-A21.3, wherein the visualizing includes blending an image derived from the test data and a video stream of the relative location of the probe.

A21.5. The method of any of paragraphs A21-A21.4, wherein the visualizing includes visualizing the test data on a head-up display.

A21.6. The method of any of paragraphs A21-A21.5, wherein the visualizing includes visualizing the test data on a head-mounted display.

A21.7. The method of any of paragraphs A21-A21.6, wherein the visualizing includes visualizing the test data on an electronic display worn by a person.

A22. The method of any of paragraphs A1-A21.7, wherein the determining the location includes wirelessly transmitting a signal related to at least one of the location of the probe relative to the test structure, the position of the probe, and the position of the test structure.

A23. The method of any of paragraphs A1-A22, wherein the acquiring the test data includes wirelessly transmitting a signal related to the test data.

A24. The method of any of paragraphs A1-A23, wherein the identifying includes wirelessly transmitting a signal related to at least one of the location of the probe relative to the test structure, the position of the probe, the position of the test structure, the test data, and the location on the test structure.

A25. The method of any of paragraphs A1-A24, wherein the associating includes correlating the test data and the location of the probe relative to the test structure.

A26. The method of any of paragraphs A1-A25, wherein the associating includes correlating a data stream including the test data and a data stream including the location of the probe.

A27. The method of any of paragraphs A1-A26, wherein the determining includes determining a plurality of locations of the probe relative to the test structure, and wherein identifying includes identifying a plurality of locations on the test structure where the test data is acquired by associating the test data and the plurality of locations of the probe relative to the test structure.

A28. The method of any of paragraphs A1-A27, wherein the determining includes recording a time when the determining is performed, wherein the acquiring includes recording a time when the acquiring is performed, and wherein the associating includes associating data recorded at substantially the same time.

A29. The method of any of paragraphs A1-A28, wherein the determining and the acquiring are performed substantially simultaneously, and wherein the associating includes associating the location of the probe with the test data acquired substantially simultaneously.

A30. The method of any of paragraphs A1-A29, wherein the determining is performed with the aid of a computer that is configured to calculate the location of the probe relative to the test structure based upon data relating to the position of the probe and to the position of the test structure, optionally wherein the computer is hand-held and/or wearable.

A31. The method of any of paragraphs A1-A30, wherein the identifying is performed with the aid of a computer that is configured to associate the location of the probe relative to the test structure with the test data acquired at that location, optionally wherein the computer is hand-held and/or wearable.

A32. The method of any of paragraphs A1-A31, wherein the determining, the acquiring test data, and the identifying are performed with the aid of a computer configured to calculate the location of the probe relative to the test structure based upon data relating to the position of the probe and to the position of the test structure, to acquire, with the probe, test data relating to the test structure, and to associate the location of the probe relative to the test structure with the test data acquired at that location, optionally wherein the computer is hand-held and/or wearable.

A33. The method of any of paragraphs A1-A32, wherein the probe is a first probe, and further comprising:

determining a location of a second probe relative to the test structure, wherein the determining includes non-contact capturing of a position of the second probe and non-contact capturing of the position of the test structure;

acquiring test data relating to the test structure with the second probe;

identifying a location on the test structure where the test data is acquired with the second probe by associating the test data acquired with the second probe and the location of the second probe relative to the test structure; and associating the test data acquired with the first probe with the test data acquired with the second probe at substantially the same location on the test structure.

B1. A non-transitory computer readable medium, comprising computer-executable instructions that, when executed, direct a computer to perform the method of any of paragraphs A1-A33.

B2. A computing device, comprising a memory device including computer-executable instructions that, when executed, direct the computing device to perform the method of any of paragraphs A1-A33.

C1. A system for non-destructive inspection of a test structure, the system comprising:

a probe configured to acquire test data relating to the test structure;

one or more electronic cameras configured to capture the position of the probe and the position of the test structure;

a computer configured to determine a location of the probe relative to the test structure based upon the captured position of the probe and the captured position of the test structure, to acquire the test data from the probe, and to identify a location on the test structure where the test data is acquired by associating the acquired test data and the location of the probe relative to the test structure; and a display configured to visualize the test data.

C2. The system of paragraph C1, wherein the display is configured to view, in conjunction with the visualized test data, at least a portion of the test structure associated with the location of the probe when the test data is acquired.

C3. The system of any of paragraphs C1-C2, wherein the display is a head-up display.

C4. The system of any of paragraphs C1-C3, wherein the display is configured to visualize, in conjunction with the visualized test data, at least a portion of the test structure associated with the location of the probe when the test data is acquired.

C5. The system of any of paragraphs C1-C4, wherein the display is a head-mounted display.

C6. The system of any of paragraphs C1-C5, wherein the computer is a wearable computer.

C7. The system of any of paragraphs C1-C6, wherein the computer includes the computing device of paragraph B2.

C8. The system of any of paragraphs C1-C7, wherein one electronic camera is configured to capture the position of the probe and the position of the test structure.

C9. The system of any of paragraphs C1-C8, further comprising: an illuminator.

C10. The system of any of paragraphs C1-C9, configured to facilitate the method of any of paragraphs A1-A33.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method of non-destructive inspection of a test structure that is an aerospace component, the method comprising:

determining a location of a hand-held probe relative to the test structure, wherein the determining includes non-contact capturing, with a head-mounted electronic camera, a position of the hand-held probe and a position of the test structure, wherein the hand-held probe includes at least one of an electrical current sensor, an electrical voltage sensor, an eddy current sensor, a sonic transducer, and an ultrasonic transducer;

acquiring, with the hand-held probe, test data relating to the test structure, wherein the test data relating to the test structure includes at least one of electrical conductivity, magnetic permeability, physical continuity, thickness, and a physical characteristic, and wherein the test data relating to the test structure relates to a presence of an anomaly;

identifying a location on the test structure where the test data is acquired by correlating the test data and the location of the hand-held probe relative to the test structure; and visualizing, on a head-mounted display, the test data in relation to the test structure;

wherein a location of the head-mounted electronic camera varies with respect to the hand-held probe and the test structure while determining the location of the hand-held probe, and wherein the determining includes compensating for variations in the location of the electronic camera.

2. A method of non-destructive inspection of a test structure that is an aerospace component, the method comprising:

determining a location of a hand-held probe relative to the test structure, wherein the determining includes non-contact capturing of a position of the hand-held probe and non-contact capturing of a position of the test structure, wherein the hand-held probe includes at least one of an electrical current sensor, an electrical voltage sensor, an eddy current sensor, a sonic transducer, and an ultrasonic transducer;

acquiring, with the hand-held probe, test data relating to the test structure, wherein the test data relating to the test structure includes at least one of electrical conductivity, magnetic permeability, physical continuity, thickness, and a physical characteristic, and wherein the test data relating to the test structure relates to a presence of an anomaly; and identifying a location on the test structure where the test data is acquired by associating the test data and the location of the hand-held probe relative to the test structure.

3. The method of claim 2, wherein the capturing the position of the probe and the capturing the position of the test structure are performed at least partially concurrently.

4. The method of claim 2, wherein the determining the location of the probe and the acquiring test data are performed at least partially concurrently.

5. The method of claim 2, wherein the determining includes using an electronic camera to determine the relative location of the probe and the test structure.

6. The method of claim 5, wherein a location of the electronic camera varies with respect to the probe and the test structure while determining the location of the probe, and wherein the determining includes compensating for variations in the location of the electronic camera.

7. The method of claim 5, wherein the using the electronic camera includes using a plurality of electronic cameras.

8. The method of claim 5, wherein the using the electronic camera includes wearing the electronic camera.

9. The method of claim 2, wherein the determining the location includes identifying a reference indicator of at least one of the probe and the test structure.

10. The method of claim 9, wherein the reference indicator is at least one of a fiducial feature and a marker.

11. The method of claim 9, wherein the probe includes a reference indicator configured to aid tracking of the probe.

12. The method of claim 9, wherein the test structure includes a reference indicator configured to aid tracking of the test structure.

13. The method of claim 2, further comprising:
adding one or more markers to the probe to aid tracking of the probe.

14. The method of claim 2, further comprising:
adding one or more markers to the test structure to aid tracking of the test structure.

15. The method of claim 2, wherein the test structure is an aerospace component forming at least part of an aerospace vehicle.

16. The method of claim 2, wherein the acquiring test data includes non-destructively measuring a property of the test structure with the probe.

17. The method of claim 2, further comprising:
visualizing the test data in relation to the test structure.

18. The method of claim 17, wherein the visualizing is performed at least partially concurrently with the acquiring test data.

19. The method of claim 2, wherein the associating includes correlating a data stream including the test data and a data stream including the location of the probe.

20. The method of claim 2, wherein the probe is a first probe, and further comprising:
determining a location of a second probe relative to the test structure, wherein the determining includes non-contact capturing of a position of the second probe and non-contact capturing of the position of the test structure;
acquiring test data relating to the test structure with the second probe;
identifying a location on the test structure where the test data is acquired with the second probe by associating the test data acquired with the second probe and the location of the second probe relative to the test structure; and
associating the test data acquired with the first probe with the test data acquired with the second probe at substantially the same location on the test structure.

21. A non-transitory computer readable medium, comprising computer-executable instructions that, when executed, direct a computer to perform the method of claim 2.

22. The method of claim 2, further comprising:
repeating the determining the location of the hand-held probe for a plurality of probe locations and recording a determination time for each probe location;
repeating the acquiring the test data for a plurality of test data points and recording an acquisition time for each test data point of the plurality of test data points; and
wherein the associating includes associating test data points and locations recorded at substantially the same time.

23. A system for non-destructive inspection of a test structure, the system comprising:
a hand-held probe configured to acquire test data relating to the test structure, wherein the test structure is an aerospace component, wherein the hand-held probe includes at least one of an electrical current sensor, an electrical voltage sensor, an eddy current sensor, a sonic transducer, and an ultrasonic transducer, wherein the test data relating to the test structure includes at least one of electrical conductivity, magnetic permeability, physical continuity, thickness, and a physical characteristic, and wherein the test data relating to the test structure relates to a presence of an anomaly;
one or more electronic cameras configured to capture the position of the hand-held probe and the position of the test structure;
a computer configured to determine a location of the hand-held probe relative to the test structure based upon the captured position of the hand-held probe and the captured position of the test structure, to acquire the test data from the hand-held probe, and to identify a location on the test structure where the test data is acquired by associating the acquired test data and the location of the hand-held probe relative to the test structure; and
a display configured to visualize the test data.

24. The system of claim 23, wherein the display is configured to view, in conjunction with the visualized test data, at least a portion of the test structure associated with the location of the probe when the test data is acquired.

25. The system of claim 23, wherein the display is configured to visualize, in conjunction with the visualized test data, at least a portion of the test structure associated with the location of the probe when the test data is acquired.

26. The system of claim 23, wherein one electronic camera is configured to capture the position of the probe and the position of the test structure.

* * * * *